(12) United States Patent
Yamane et al.

(10) Patent No.: US 8,404,868 B2
(45) Date of Patent: Mar. 26, 2013

(54) METHOD FOR PURIFICATION OF CYCLIC ESTER

(75) Inventors: Kazuyuki Yamane, Iwaki (JP); Tomohiro Hoshi, Iwaki (JP); Tomoyuki Ogawa, Iwaki (JP)

(73) Assignee: Kureha Corporation, Tokyo (JP)

( * ) Notice: Subject to any disclaimer, the term of this patent is extended or adjusted under 35 U.S.C. 154(b) by 633 days.

(21) Appl. No.: 12/449,669

(22) PCT Filed: Jan. 28, 2008

(86) PCT No.: PCT/JP2008/051229
§ 371 (c)(1),
(2), (4) Date: Dec. 28, 2009

(87) PCT Pub. No.: WO2008/102607
PCT Pub. Date: Aug. 28, 2008

(65) Prior Publication Data
US 2010/0168446 A1    Jul. 1, 2010

(30) Foreign Application Priority Data
Feb. 20, 2007 (JP) ................................. 2007-039368

(51) Int. Cl.
*C07D 321/00* (2006.01)
*C07D 319/00* (2006.01)
(52) U.S. Cl. ........................................ 549/267; 549/274
(58) Field of Classification Search .................. 549/267, 549/274
See application file for complete search history.

(56) References Cited

U.S. PATENT DOCUMENTS

| | | | |
|---|---|---|---|
| 5,266,706 A * | 11/1993 | Bhatia | 549/274 |
| 5,830,991 A | 11/1998 | Shiiki et al. | |
| 2003/0191326 A1 * | 10/2003 | Yamane et al. | 549/267 |

FOREIGN PATENT DOCUMENTS

| | | |
|---|---|---|
| EP | 1273579 A1 | 1/2003 |
| EP | 1310496 A1 | 5/2003 |
| JP | 09-328481 A | 12/1997 |
| JP | 2001-278877 A | 10/2001 |
| WO | WO02/14303 A1 | 2/2002 |

OTHER PUBLICATIONS

Christian Reichardt, Solvents and Solvent Effects in Organic Chemistry, 3rd. ed., 2003,Wiley-VCH Verlag GmbH Co. KGaA, Weinheim, p. 1-37.*
"Solvent Handbook", published by K.K. Koudansha; 1985: vol. 6, pp. 149-152.
Kagaku Jikken Sousahou (Operation Methods in Chemical Experiments); published by K.K. Nankoudou; 1963; vol. 1; pp. 223,229,230 and 234.

* cited by examiner

*Primary Examiner* — Taylor Victor Oh
(74) *Attorney, Agent, or Firm* — Wenderoth, Lind & Ponack, L.L.P.

(57) ABSTRACT

A method of purifying a cyclic ester, comprising: mixing a co-distillated liquid comprising a cyclic ester produced by heating depolymerization of a hydroxycarboxylic acid oligomer in the presence of a depolymerization solvent and the depolymerization solvent with an organic solvent for washing which is mutually soluble with the depolymerization solvent and has a lower boiling point than the cyclic ester; subjecting the resultant mixture liquid to liquid-liquid separation into an organic solvent phase containing the depolymerization solvent and a cyclic ester phase containing the organic solvent; and then evaporating the organic solvent from the cyclic ester phase containing the organic solvent to recover the cyclic ester containing a reduced amount of the depolymerization solvent. As a result, purified cyclic ester is recovered at high heat efficiency, purification efficiency and operation efficiency, from the co-distillate liquid containing the depolymerization solvent and the cyclic ester from the depolymerization system for thermal decomposition of the hydroxycarboxylic acid oligomer in the presence of the depolymerization solvent.

9 Claims, No Drawings

METHOD FOR PURIFICATION OF CYCLIC ESTER

This application is the United States national stage of International Application No. PCT/JP2008/051229, filed Jan. 28, 2008, which was published as International Publication No. WO 2008/102607A1, and which claims benefit of Japanese Patent Application No. 039368/2007, filed Feb. 20, 2007, and the text of application 039368/2007, is incorporated by reference in its entirety herewith.

TECHNICAL FIELD

The present invention relates to an improvement in method for purification of a cyclic ester produced by heating depolymerization of a hydroxycarboxylic acid oligomer.

BACKGROUND ART

There is known a process for producing a cyclic ester, such as glycolide or lactide, by heating depolymerization of oligomer of a hydroxycarboxylic acid, such as glycolic acid or lactic acid, in the presence of a polyalkylene glycol-type depolymerization solvent (Patent document 1).
It has been also disclosed that the resultant cyclic ester is distilled together with depolymerization solvent, and the cyclic ester precipitated from the distillate liquid is separated and purified by adding a non-solvent for the cyclic ester, as desired, or the cyclic ester phase separated from the depolymerization solvent phase in the distillate is recovered by liquid-liquid separation (Patent document 1). Alternatively, there are also known a method of cyclic ester by recrystallization from an organic solvent, such as ethyl acetate (Patent document 1), and a method of washing the cyclic ester precipitated from the distillate by washing with an organic solvent, such as cyclohexanone or ethyl acetate, mutually soluble with the depolymerization solvent (Patent document 2). According to these methods of purification of cyclic esters, however, it is difficult to obtain a high-purity cyclic ester suitable as a starting material for bulk-polymerization for production of a high polymerization-degree of polyhydroxy carboxylic acid, such as polyglycolide (polyglycolic acid) or polylactide (polylactic acid). According to recrystallization from an organic solvent, it is possible to obtain a cyclic ester of high purity, but generally recrystallization is inefficient from the viewpoint of either energy or yield, and it is hard to commercially adopt it as a main method of purification of cyclic ester.

Patent document 1: WO 02/14303A1,
Patent document 2: JP-A2001-278877

DISCLOSURE OF INVENTION

In view of the above-mentioned circumstances, a principal object of the present invention is to provide a commercially feasible method of purifying a cyclic ester produced by heating depolymerization of a hydroxycarboxylic acid oligomer.

According to the present inventors' study for achievement of the above-mentioned object, it was found very effective to adopt washing with an organic solvent selected separately from the depolymerization solvent and evaporation-removal of the organic solvent. Thus, according to the present invention, there is provided a method of purifying a cyclic ester, comprising: mixing a co-distillated liquid comprising a cyclic ester produced by heating depolymerization of a hydroxycarboxylic acid oligomer in the presence of a depolymerization solvent and the depolymerization solvent with an organic solvent for washing which is mutually soluble with the depolymerization solvent and has a lower boiling point than the cyclic ester; subjecting the resultant mixture liquid to liquid-liquid separation into an organic solvent phase containing the depolymerization solvent and a cyclic ester phase containing the organic solvent; and then evaporating the organic solvent from the a cyclic ester phase containing the organic solvent to recover the cyclic ester containing a reduced amount of the depolymerization solvent.

In a preferred embodiment of the present invention, prior to the step of mixing the co-distillated liquid including the cyclic ester and the depolymerization solvent with the organic solvent for washing, the co-distillated liquid is subjected to liquid-liquid separation into a depolymerization solvent phase and a cyclic ester phase containing the depolymerization solvent, and the resultant cyclic ester phase containing the depolymerization solvent is washed by mixing with the organic solvent. The liquid-liquid separation of the depolymerization solvent phase and the crude cyclic ester phase can be carried out by using the energy of the co-distillate per se from the depolymerization system, without additional heat supply from the outside. Further, for the washing of the cyclic ester liquid containing the depolymerization solvent with a low-boiling point organic solvent mutually soluble with the depolymerization solvent, a liquid-liquid mixing process at a good contact efficiency can also be adopted to attain a high efficiency for removal of the depolymerization solvent, and also for a subsequent removal by evaporation of the low-boiling point organic solvent, a minimum external heat supply of supplying heat for evaporation of the organic solvent is necessary, whereby an effective method of purification of a cyclic ester with a very high thermal efficiency as a whole can be realized. Moreover, since the purification is carried out generally in the liquid state and with minimum handling of solid matter, the processed materials can be advantageously handled efficiently.

BEST MODE FOR PRACTICING THE INVENTION

Hereinafter, the present invention will be described more specifically with reference to preferred embodiments thereof. In the following description, "%" and "ppm" used about quantitative ratios, contents, or purity are on a weight basis, unless otherwise mentioned specifically.

The co-distillate from the depolymerization system containing a depolymerization solvent and a cyclic ester resultant after the heating depolymerization of a hydroxycarboxylic acid oligomer in the presence of a depolymerization solvent, as an object to be treated by the method of purification of a cyclic ester according to the present invention, is not essentially different from what is disclosed in the above-mentioned Patent document 1. Accordingly, general features of the co-distillate are described hereinbelow, while mainly summarizing the description of Patent document 1.

(Cyclic Ester and Aliphatic Polyester)
As the cyclic ester, intermolecular cyclic esters, i.e., bimolecular cyclic esters, of α-hydroxycarboxylic acids, such as glycolic acid, lactic acid, α-hydroxybutyric acid, and α-hydroxy-valeric acid, may be used. For example, the bimolecular cyclic ester of glycolic acid is glycolide, and the bimolecular cyclic ester of lactic acid is lactide (D-lactide and/or L-lactide).

Examples of the hydroxycarboxylic acid oligomer as starting materials for production of cyclic esters by heating depolymerization, may include: oligomers of α-hydroxycarboxylic acids, such as glycolic acid, lactic acid, and butyric acid.

The hydroxycarboxylic acid oligomer may include at least 2, preferably at least 5, repeating units (—O—R—CO—) of the hydroxycarboxylic acid. In other words, the oligomer can be one of a low polymerization degree but may suitably be one having a melting point (Tm) of ordinarily at least 140° C., preferably at least 160° C., more preferably at least 180° C., from the viewpoint of the yield of a cyclic ester, such as a glycolide, in the depolymerization. Here, Tm refers to an endothermic peak temperature detected by using a differential scanning calorimeter (DSC) at a temperature increase rate of 10° C./min. in an inert gas atmosphere.

On the other hand, from a viewpoint of the ease of oligomer production, an oligomer having a weight-average molecular weight (as measured by gel-permeation-chromatography (GPC) using a hexafluoroisopropanol (HFIP) solvent and polymethyl methacrylate as the molecular weight standard substance) of at most 40,000, preferably at most 30,000, may generally be used.

Various α-hydroxycarboxylic acid oligomers may be obtained, e.g., by polycondensation of an α-hydroxycarboxylic acid, its alkyl ester (having an alkyl group of ca.1-4 carbon atoms), or its salt in the presence of a catalyst, as desired.

More specifically, for the synthesis of glycolic acid oligomer used as a starting material of glycolide, glycolic acid, its ester, or a salt, may be subjected to condensation or transesterification in the presence of a condensation catalyst or a transesterification catalyst, as desired, under a reduced pressure or an elevated pressure, under heating at a temperature of 100-250° C., preferably 140-230° C., until substantially no distillate of low molecular weight substances, such as water and an alcohol, is found. After the completion of the condensation or transesterification, the resultant oligomer may be used as it is as a starting material. Alternatively, the obtained oligomer can be taken out from a reaction system and washed with a non-solvent, such as benzene or toluene to remove an unreacted material, a catalyst, etc., before it is used. The oligomer may have a structure of either a cyclic form or a chain form (straight or branched). A linear oligomer may have an advantage of easy synthesis, and a branched oligomer may have a characteristic of a relatively low melting point. Other α-hydroxycarboxylic acid oligomers may be synthesized by similar processes.

(Depolymerization Solvent)

As the depolymerization solvent, it is suitable to use a polyalkylene glycol ether represented by a formula (1) below and has a boiling point of 230-450° C. (under normal pressure) and a molecular weight of 150-450:

$$X^1-O-(R^1-O)_p-Y \quad (1)$$

(wherein R1 denotes a methylene group or a linear or branched alkylene group of 2-8 carbon atoms; X1, a hydrocarbon group; Y, an alkyl group or aryl group of 2-20 carbon atoms; p, an integer of at least 1; and when p is 2 or more, two or more R1 groups may be the same or different).

The polyalkylene glycol ether is used as a polar organic solvent for the de- polymerization of the hydroxycarboxylic acid oligomer, and is taken out from the reaction system by co-distillation with the produced cyclic ester, such as glycolide.

If the boiling point of the polyalkylene glycol ether is too low, it becomes impossible to set a high depolymerization temperature and the rate of production of a cyclic ester is caused to be lowered. On the other hand, if the boiling point of polyalkylene glycol ether is too high, it becomes difficult to distill the polyalkylene glycol ether, and the co-distillation with the cyclic ester produced according to the depolymerization becomes difficult. The polyalkylene glycol ether may have a boiling point (under normal pressure) in the range of preferably 235-450° C., more preferably 240-430° C., most preferably 250-420 ° C.

The polyalkylene glycol ether has a molecular weight of 150-450. If the molecular weight of polyalkylene glycol ether is either too low or too high, the co-distillation thereof with a cyclic ester, such as a glycolide, becomes difficult. The molecular weight of the polyalkylene glycol ether is preferably 180-420, more preferably 200-400.

In the above formula (1), X1 is a hydrocarbon group, including an alkyl group, an aryl group, etc. as specific examples.

In case where the sum of the numbers of carbon atoms of the ether oxygen linkage groups (X1 and Y) at both ends of the polyalkylene glycol ether exceeds 21, it becomes difficult to form a uniform molten liquid phase together with the hydroxycarboxylic acid oligomer at the time of the depolymerization.

It is desirable that each of the ether oxygen linkage groups (X1 and Y) at both ends is an alkyl group and the sum of the number of carbon atoms of these alkyl groups is in the range of 3-21, preferably 6-20, for the polyalkylene glycol ether. Examples of such an alkyl group may include: a propyl group, a butyl group, a pentyl group, a hexyl group, a heptyl group, an octyl group, a nonyl group, a decyl group, and a lauryl group. These alkyl groups may be either linear or branched.

As the polyalkylene glycol dialkyl ether, polyethylene glycol dialkyl ethers are preferred, and among these, diethylene glycol dialkyl ether, triethylene glycol dialkyl ether, and tetraethylene glycol dialkyl ether are further preferred.

Two ether oxygen-bonded alkyl groups at both ends of the polyalkylene glycol ether, may have the same number of carbon atoms so as to provide, e.g., dibutyl, dihexyl, and dioctyl, but the same number of carbon atoms is not essential, and the combination of different alkyl groups, e.g., combinations of a propyl group and a lauryl group, a hexyl group and a heptyl group, and a butyl group and an octyl group, may also be used.

The property of the polyalkylene glycol ether may also vary with the number of repetition p of the alkylene-oxy unit (—R1-O—) in the formula (1). In the present invention, it is preferred to use a polyalkylene glycol ether having a number of repetition p of 2-8, preferably 2-5. As the number of repetition p becomes larger, the distribution of polymerization degree is liable to be broader at the time of synthesis by a polyaddition reaction, and it becomes difficult to isolate the polyalkylene glycol ether of an identical number of the repeating units. If the number of repeating unit p exceeds 8 particularly, isolation by distillation thereof will also become difficult because of a high-molecular weight, thus resulting in a lower yield.

The alkylene oxy unit (—R1-O—) is not particularly restricted, as far as R1 is a methylene group or a linear or branched alkylene group of 2-8 carbon atoms, and examples thereof may include: polyethylene glycol ether having ethylene-oxy unit of 2 carbon atoms in R1, polypropylene glycol ether including the propylene-oxy unit of 3 carbon atoms in R1, and polybutylene glycol ether including butylene-oxy unit of 4carbon atoms in R1. Among these, polyethylene glycol ether is particularly preferred because of easiness of obtaining a starting material and easiness of synthesis.

The polyalkylene glycol ether may preferably provide a solubility of a cyclic ester, such as a glycolide, therein of at least 0.1% at 25° C. In many cases, it is preferred to use a polyalkylene glycol ether providing a solubility of cyclic ester in the range of 0.1 to 10%. Herein, the solubility of cyclic ester at 25° C. is measured as a percentage by mass of cyclic ester B (g) with respect to the volume A (mL) of polyalkylene glycol ether when a cyclic ester, such as glycolide, is dissolved up to its saturation in polyalkylene glycol ether at 25° C. More specifically, the solubility is shown by a formula below:

Solubility (%)=($B/A$)×100.

If the solubility is too low, the cyclic ester, such as a glycolide, co-distilled with the polyalkylene glycol ether is liable to be precipitated to result in undesirable blocking of the recovery line, etc. If the solubility is too high, when the cyclic ester is recovered from the co-distillate liquid obtained by the depolymerization by liquid-liquid separation, it will be necessary to cool the co-distillate down to a temperature of 0° C. or below, or to add a non-solvent in order to isolate the cyclic ester.

(Solubilizing Agent)

In order to improve the dissolution property (solubility and/or dissolution rate) of hydroxycarboxylic acid oligomers, such as a glycolic acid oligomer in the polyalkylene glycol ether, a solubilizing agent may be included in a heating depolymerization system.

Preferred properties of the solubilizing agent may include: (i) non-basicity so as to be little liable to react with the cyclic ester, (ii) mutual solubility with both the polyalkylene glycol ether as the depolymerization solvent and the hydroxycarboxylic acid oligomer as the starting material, preferably a larger affinity to the hydroxycarboxylic acid oligomer, and (iii) a boiling point higher than a depolymerization solvent, preferably a boiling point of at least 450° C. Among specific examples of the solubilizing agent, monohydric or polyhydric alcohols are preferred among others, including particularly polyalkylene glycols represented by formula (2) below or polyalkylene glycol mono-ethers represented by formula (3) below:

(2)

(wherein R2 denotes a methylene group or a linear or branched alkylene group of 2-8 carbon atoms, q denotes an integer of at least 1, and when q is at least 2, two or more R2 may be the same or different);

(3)

(wherein R3 denotes a methylene group or a linear or branched alkylene group of 2-8 carbon atoms, X2 denotes a hydrocarbon group, r denotes an integer of at least 1, and when r is at least 2, two or more R3 may be the same or different).

Specific examples of the polyalkylene glycol may include: polyethylene glycol, polypropylene glycol, and polybutylene glycol.

Specific examples of the polyalkylene glycol mono-ether may include: polypropylene glycol mono-methyl ether, polyethylene glycol mono-ethers, such as polyethylene glycol mono-propyl ether, polyethylene glycol mono-butyl ether, polyethylene glycol mono-hexyl. ether, polyethylene glycol mono-octyl ether, polyethylene glycol mono-decyl ether and polyethylene glycol mono-lauryl ether; polyalkylene glycol mono-ethers, such as polypropylene glycol mono-ethers and polybutylene glycol mono-ethers obtained by replacing the ethylene-oxy group with propylene-oxy group or butylene-oxy group in the above-mentioned polyethylene glycol mono-ethers; etc. The polyethylene glycol mono-ethers may preferably have an ether group including an alkyl group of 1-18 carbon atoms, more preferably 6-18 carbon atoms. These compounds may respectively be used singly or in combination of two or more species.

The solubilizing agent, when used, may be used in a proportion of ordinarily 0.1 to 500 wt. parts, preferably one to 300 wt. parts per 100 wt. parts of the hydroxycarboxylic acid oligomer.

(Heating Depolymerization)

The process for production of a cyclic ester by heating de-polymerization of a hydroxycarboxylic acid oligomer may include the following steps:

(I) a step of heating a mixture containing the hydroxycarboxylic acid oligomer and the depolymerization solvent to a temperature of at least 200° C. causing depolymerization of the hydroxycarboxylic acid oligomer under normal pressure or a reduced pressure, (II) a step of forming a liquid phase wherein a molten liquid phase of the hydroxycarboxylic acid oligomer and the depolymerization solvent form a substantially uniform phase, (III) a step of continuing the heating in the solution state to distil off the cyclic ester produced by depolymerization together with the de-polymerization solvent, and (IV) a step of recovering the cyclic ester from the distillate.

A preferred mode of production process performed as a preceding stage of the method of purification of a cyclic ester of the present invention is most characterized by performing the depolymerization of an aliphatic polyester in a solution phase. Although the depolymerization is ordinarily performed at a temperature of at least 200° C., if most of the aliphatic polyester is not dissolved but forms a molten liquid phase, the cyclic ester cannot be distilled easily and, moreover, the molten liquid phase is liable to become heavier. By heating a greater portion of aliphatic polyester in a solution phase state, the generation and vaporization speeds of the cyclic ester are increased remarkably.

Depolymerization caused in the above-mentioned step (III) is basically a reaction represented by the following reaction-formula [III], when polyglycolic acid (polyglycolide) is taken for an example.

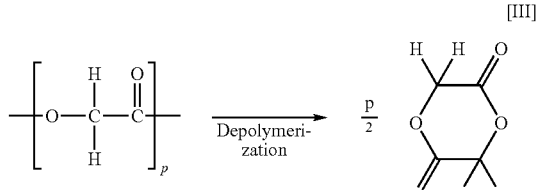

[III]

The heating temperature for the depolymerization is at or above a temperature at which depolymerization of the aliphatic polyester takes place, and is usually at least 200° C. The heating temperature is in the range of ordinarily 200-320° C., preferably 210-310° C., more preferably 220-300° C., particularly preferably 230-290° C.

By the heating, the depolymerization of a hydroxycarboxylic acid oligomer occurs and a cyclic ester, such as a glycolide (boiling point: 240-241° C. under an atmospheric pressure), is distilled together with the solvent. As the depolymerization is a reversible reaction, the depolymerization advances efficiently by distilling off a cyclic ester, such as a glycolide, from the liquid phase.

The heating for the depolymerization may be performed under normal pressure or a reduced pressure, but may preferably be performed under a reduced pressure of 0.1-90 kPa. A lower pressure leads to a lower depolymerization temperature and a higher rate of recovery of the solvent. The pressure is preferably 1-50 kPa, more preferably 3-30 kPa, particularly preferably 5-20 kPa.

The polyalkylene glycol ether used as a depolymerization solvent may be used at a rate of ordinarily 30-500 wt. parts, preferably 50-200 wt. parts, per 100 wt parts of aliphatic polyester. The polyalkylene glycol ether may be added continuously or in division in an intermediate stage during the depolymerization as far as the mixture in the reaction system forms a substantially uniform liquid phase. Further, in order to form a more uniform liquid phase, a solubilizing agent may be added into the mixture, and the solubilizing agent may also be added continuously or in division during the depolymerization.

From the co-distillated mixture liquid of a cyclic ester and a depolymerization solvent thus-obtained from the heating depolymerization system in the above-described manner, a purified cyclic ester is, recovered in accordance with the method of the present invention.

(Liquid-Liquid Separation of a Depolymerization Solvent and a Crude cyclic Ester)

For the above purpose, it is also possible to mix for washing the co-distillated mixture liquid directly with a later-described organic solvent (organic solvent for washing) which is mutually soluble with the depolymerization solvent and has a lower boiling point than the cyclic ester, but in order to reduce the amount of the organic solvent used for washing, it is preferred to include a step of subjecting the co-distillate from the heating depolymerization system first to liquid-liquid separation into a depolymerization solvent phase and a crude cyclic ester phase containing the depolymerization solvent.

More specifically, the distillate from the heating depolymerization system is cooled with a cooler (condenser), to cause a phase separation into a cyclic ester, such as glycolide, and the solvent, while maintaining the liquid phase. As a result of the phase separation, the distillate is usually separated into a lower layer of the cyclic ester phase, and an upper layer of the solvent phase. The lower layer cyclic ester phase can be recovered in separation while maintaining its liquid state. In order to effect the phase separation into the cyclic ester and the solvent, the cooling temperature is controlled ordinarily at 85-180° C., preferably at 85-150° C., more preferably at 85-120° C. If the cooling temperature is too high, side reactions, such as a ring-opening reaction and a polymerization reaction, are liable to occur in the cyclic ester phase during the separation operation. If the cooling temperature is too low, it becomes difficult to effect the phase separation while maintaining the liquid state.

If the depolymerization is continued under a temperature control of the distillate by a condenser, the cyclic ester distilled together with the solvent is caused to pass through the upper solvent phase while forming droplets to be condensed into the lower layer cyclic ester phase.

In order to effect such phase separation, it is preferred to use as a depolymerization solvent a polyalkylene glycol ether comprising ether oxygen-bonded alkyl groups at both ends thereof including a total of 3-21 carbon atoms in the alkyl groups. Such a solvent can be easily separated from the cyclic ester, such as glycolide, at the above-mentioned cooling temperature.

Although a small amount (e.g., ca. 0.1-10 wt. %) of cyclic ester is dissolved in the polyalkylene glycol ether as the depolymerization solvent separated into the upper layer, substantially the whole quantity thereof can be returned to the depolymerization system without passing through steps, such as purification, since all the components therein are retained in a thermally stable state. According to this method, it becomes unnecessary to recover a lot of solvent, and it becomes unnecessary to prepare the solvent in a quantity exceeding a level determined based on the volume of the reaction vessel. Therefore, by this method, the loss of the depolymerization solvent can be suppressed to the minimum.

(Washing of the Cyclic Ester)

The cyclic ester separated from the depolymerization solvent phase through the above-mentioned liquid-liquid separation step still contains ca. 0.05 to 2% of depolymerization solvent, and if the cyclic ester is subjected to ring-opening polymerization as it is, it is difficult to obtain an aliphatic polyester (polyhydroxy carboxylic acid) of a high-molecular weight. Therefore, in accordance with the method of the present invention, the crude cyclic ester liquid containing such a depolymerization solvent is washed with an organic solvent which is mutually soluble with the depolymerization solvent and has a lower boiling point than the cyclic ester.

(Organic Solvent for Washing)

The organic solvent for washing is an organic solvent which has a mutual solubility with the polyalkylene glycol ether used as the depolymerization solvent, and also a lower boiling point that the cyclic ester, such as glycolide (ca. 85° C. of melting point, ca. 240° C. of boiling point), and lactide (ca. 95° C. of melting point, ca. 142° C. (under a reduced pressure of 8 mmHg-absolute) of boiling point). Preferred examples thereof may include: saturated aliphatic hydrocarbons, such as hexane (boiling point: ca. 69° C.) and heptane (boiling point: ca. 98° C.); alicyclic hydrocarbons, such as cyclohexane (boiling point: ca. 81° C.); ethers, such as diisopropyl ether (boiling point: ca. 68° C.); etc., and also mixtures of these. Among these, saturated aliphatic hydrocarbons, such as hexane, which are excellent in thermal stability and mutual solubility with the depolymerization solvent, or a mixture of these, are used particularly preferably.

The washing with the organic solvent has to be performed at a temperature capable of maintaining the molten-liquid state of crude cyclic ester, preferably 85-150° C., more preferably 90-130° C., in order to maintain a high efficiency of washing accompanied optionally by stirring which is mechanical or by way of bubbling, etc., and under pressurization, as needed, in order to suppress the evaporation of the organic solvent for washing at the temperature. Moreover, the organic solvent may preferably have a boiling point (under normal pressure) of 90° C. or less, particularly 80° C. or less, in order to facilitate the separation removal by evaporation thereof from the cyclic ester after the washing.

Cyclic ester is recovered from the liquid mixture of the cyclic ester and the organic solvent after the washing, by removing the organic solvent by evaporation. In this instance, in order to reduce the evaporation load of the organic solvent and also the amount of depolymerization solvent accompanying the cyclic ester, it is preferred to once subject the liquid mixture of the cyclic ester and the organic solvent after the washing to liquid-liquid separation into an upper layer of the organic solvent phase and a lower layer of the cyclic ester phase. Then, the organic solvent is recovered from the organic solvent phase containing the depolymerization solvent transferred from the cyclic ester phase, by distillation etc., and the remaining depolymerization solvent may be refined and recovered, or disposed as a waste.

From the cyclic ester phase separated from the organic solvent phase, the organic solvent for washing of a low boiling point can be removed easily and efficiently by evaporation utilizing a boiling point difference from the cyclic ester. The organic solvent removal efficiency can be improved by performing it under a reduced pressure, or with bubbling with an inert gas, etc, as needed.

The thud-refined cyclic ester having separated the organic solvent is already suitable for production of an aliphatic polyester (polyhydroxy carboxylic acid) by bulk polymerization, but it is also preferred to further refine it for aiming at production of an aliphatic polyester of a higher-molecular weight.

A preferred embodiment of such further refining is a method for purification of a cyclic ester as already proposed by a research group of the present inventors, including the use of a column-type crystal refiner comprising two cylindrical columns combined and superposed with each other so as to have their central axes extend in parallel with each other, supplying a crude cyclic ester from the bottom of the refiner to cause the crude cyclic ester to ascend under stirring and contact countercurrently a descending relatively purified cyclic ester, thereby performing the refining of the crude cyclic ester, and withdrawing a molten liquid of purified cyclic ester from the column top while withdrawing impurities from the bottom of the refiner (JP-A 2001-278877).

The present inventors have further found it very effective to subject the refined cyclic ester having separated the organic solvent in the above-described manner further to crystallization, and after solid-liquid separation, subjecting the solid to washing with a molten liquid of refined cyclic ester for the production of a cyclic ester of a higher purity.

The purified cyclic ester obtained through the above-mentioned series of steps can acquire a purity of at least 99.9 mol %, a residual depolymerization solvent content of 10 ppm or less, and a residual washing organic solvent content of 10 ppm or less, so that it is particularly suitable for production of an aliphatic polyester of a high degree of polymerization through bulk polymerization.

For the production of an aliphatic polyester by bulk polymerization of the purified cyclic ester obtained through the method of the present invention, conventional processes can be arbitrarily adopted. For example, it is possible to suitably adopt a process for producing an aliphatic polyester, comprising: subjecting a cyclic ester containing water and an alcohol as initiators or/and molecular weight-adjusting agents to ring-opening polymerization based on a total proton concentration and a ratio (carboxylic acid/ester mol ratio) between a mol concentration of carboxyl (carboxylic acid)-source compounds including water and a mol concentration of alkoxy-carbonyl (ester)-source compounds, as polymerization-controlling indexes (WO 2005/044894A1).

EXAMPLES

Hereinbelow, the present invention will be described more specifically based on Examples and Comparative Examples. First, analysis methods adopted for evaluation of Examples and Comparative Examples are described.
<<Analysis methods>>
[Depolymerization Solvent Concentration]
About 40 mg of 4-chlorobenzophenone as an internal standard substance was added to 300 mg -1000 mg of a cyclic ester (glycolide) sample and dissolved in 10 mL of dimethyl ether. 1 µL of the solution was sampled and injected into a GC apparatus to measure a depolymerization solvent concentration in the sample.
(GC Analysis Conditions)
Equipment: Shimadzu "GC-2010"
Column: "TC-17"(0.25 mm-dia.x30 m)
Column temperature: Held at 220° C. for 20 minutes.
Gasification chamber temperature: 200° C.
Detector: FID (hydrogen flame ionization detector)
Temperature: 300° C.
[Concentration of Organic Solvent for Washing]
About 40 mg of 4-chlorobenzophenone as an internal standard substance was added to 1000 mg of a cyclic ester (glycolide) sample and dissolved in 10 mL of dimethylformamide. 1 µL of the solution was sampled and injected into a GC apparatus to measure a concentration of organic solvent for washing (hexane) in the sample.
(GC Analysis Conditions)
Apparatus: Shimadzu "GC-2010"
Column: "TC-17" (0.25 mm-dia.x30 m)
Column temperature: Held at 50° C. for 5 minutes, increase to 270° C. at a rate of 20° C/min. and held at 270° C. for 4 minutes.
Gasification chamber temperature: 200° C.
Detector: FID (hydrogen flame ionization detector)
Temperature: 300° C.
[Glycolide Purity]
For a sample of a low purity (below ca. 98 mol %), by a GC method similarly as in the measurement of [Depolymerization solvent concentration] described above, 300-1000 mg each of a pure glycolide sample and an impurity-containing glycolide sample respectively containing ca. 40 mg of chlorobenzophenone were separately injected into a GC apparatus, respectively, to measure a glycolide purity (wt. %) in terms of an areal ratio of a relative area of a glycolide peak with respect to an internal standard peak in the impurity-containing sample to a relative area of a glycolide peak to an internal standard peak in the pure glycolide sample.

For a sample of a high purity (at least 98 mol %), a DSC purity (mole %) measurement was performed based on a melting point lowering from the pure substance due to an impurity content based on the van't Hoff's law (formula (1) below):

$$T_f = T_0 - X_2 \cdot R \cdot T_0^2 / \Delta H_f \qquad (1),$$

wherein $T_f$=equilibrium melting point during fusion (K), $T_0$=melting point of main pure substance (glycolide) (K), $X_2$=a total mole fraction of impurities in the liquid phase (–), R=gas constant=8.31 J/mol-K, and $\Delta H_f$=heat of fusion of main pure substance (glycolide) (J/mol).

In the measurement, a DSC apparatus ("DSC20/TC 10A" made by Mettler-Toledo Co.) was used, and an accurately weighed ca. 10-mg of an impurity-containing glycolide sample was hermetically sealed in an aluminum pan (ca. 40µL)) and subjected to heating at a rate of 2° C./min. in a temperature range of 70-95° C. to measure a melting peak of glycolide, thereby measuring a total molar fraction X2 of the impurities in the above-mentioned formula (1) and obtaining a glycolide purity (mole %) according to a formula of: 100–100·X2.

Example 1

[Step 1]
Into a 500 mL-flask, 160 g of glycolic acid oligomer (weight-average molecular weight: ca. 15,000), 100 g of diethylene glycol dibutyl ether (DEG-DB) as a depolymerization solvent, and 88.9 g of polyethylene glycol #300 as a solubilizing agent, were supplied and then heated to 260° C.

under a reduced pressure of 20 kPa to effect a depolymerization reaction. The resultant glycolide was distilled off together with the DEG-DB, and after being condensed by cooling to 85° C. with a cooler, left standing to cause liquid—liquid separation, and the separated DEG-DB was caused to overflow from the liquid-liquid separation vessel and continuously returned into the flask. The glycolide collected at a lower part of the separation vessel was withdrawn once per hour (ca. 30 g per once). Further, pulverized glycolic acid oligomer in an amount equal to the recovered glycolide was charged to an oligomer melting vessel and, after being heat-melted at 220° C., was added into the flask to continue the depolymerization reaction. The above operation was continued for 30 hours, and a total of 1000-g glycolide was obtained. The recovered glycolide contained 4,500 ppm of DEG-DB.

[Step 2]

After mixing the recovered glycolide with an equal weight (1000 g) of hexane at 90° C., the mixture was left standing to cause liquid-liquid separation, whereby 980 g of lower layer glycolide was recovered. Incidentally, since it was a higher temperature than the boiling point (69° C.) of hexane, the operation was performed in a hermetically closed container so as to prevent the evaporation of hexane. The recovered glycolide contained 900 ppm of DEG-DB and 4,200 ppm of hexane.

[Step 3]

The glycolide obtained in Step 2 was subjected to 5 minutes of bubbling with N2 gas under the condition of 90° C. The DEG-DB concentration in the glycolide after the bubbling was 900 ppm, and the hexane concentration was 30 ppm.

Example 2

[Step 1]

A similar operation as in Example 1 was performed except that triethylene glycol butyl hexyl ether (TEG-BH) was used as a depolymerization solvent and the depolymerization was performed under a reduced pressure of 15 kPa. Totally 1000 g of glycolide was obtained in 30 hours of operation. 4,500 ppm of TEG-BH was contained in the recovered glycolide.

[Step 2]

When a similar operation as in Example 1 was performed, the TEG-BH concentration in the recovered glycolide was 2,200 ppm, and the hexane concentration was 4,000 ppm.

[Step 3]

When a similar operation as in Example 1 was performed, the TEG-BH concentration in the glycolide after the bubbling was 2,200 ppm, and the hexane concentration was 30 ppm.

Example 3

[Step 1]

A similar operation as in Example 1 was performed except that triethylene glycol butyl octyl ether (TEG-BO) was used as a depolymerization solvent and the depolymerization was performed under a reduced pressure of 10 kPa. Totally 1000 g of glycolide was obtained in 30 hours of operation. 3,900 ppm of TEG-BO was contained in the recovered glycolide.

[Step 2]

When a similar operation as in Example 1 was performed, the TEG-BO concentration in the recovered glycolide was 270 ppm, and the hexane concentration was 4,000 ppm.

[Step 3]

When a similar operation as in Example 1 was performed, the TEG-BO concentration in the glycolide after the bubbling was 290 ppm, and the hexane concentration was 30 ppm.

Example 4

[Step 1]

A similar operation as in Example 1 was performed except that triethylene glycol butyl decyl ether (TEG-BD) was used as a depolymerization solvent and the depolymerization was performed under heating up to 280° C. and a reduced pressure of 8 kPa. Totally 1000 g of glycolide was obtained in 30 hours of operation. 700 ppm of TEG-BD was contained in the recovered glycolide.

[Step 2]

When a similar operation as in Example 1 was performed, the TEG-BD concentration in the recovered glycolide was 400 ppm, and the hexane concentration was 4,200 ppm.

[Step 3]

When a similar operation as in Example 1 was performed, the TEG-BD concentration in the glycolide after the bubbling was 410 ppm, and the hexane concentration was 30 ppm.

Example 5

[Step 1]

A similar operation as in Example 1 was performed except that diethylene glycol butyl 2-chlorophenyl ether (DEG-BClPh) was used as a depolymerization solvent and the depolymerization was performed under heating up to 280° C. and a reduced pressure of 8 kPa. Totally 1000 g of glycolide was obtained in 30 hours of operation. 16,000 ppm of DEG-BClPh was contained in the recovered glycolide.

[Step 2]

When a similar operation as in Example 1 was performed, the DEG-BClPh concentration in the recovered glycolide was 4,500 ppm, and the hexane concentration was 4,000 ppm.

[Step 3]

When a similar operation as in Example 1 was performed, the DEG-BClPh concentration in the glycolide after the bubbling was 4,500 ppm, and the hexane concentration was 30 ppm.

Example 6

[Step 1]

A similar operation as in Example 1 was performed except that triethylene glycol dibutyl 2-chlorophenyl ether (TEG-DB) was used as a depolymerization solvent and the depolymerization was performed under heating up to 280° C. and a reduced pressure of 10 kPa. Totally 1000 g of glycolide was obtained in 30 hours of operation. 10,000 ppm of TEG-DB was contained in the recovered glycolide.

[Step 2]

When a similar operation as in Example 1 was performed, the TEG-DB concentration in the recovered glycolide was 1,500 ppm, and the hexane concentration was 4,000 ppm.

[Step 3]

When a similar operation as in Example 1 was performed, the TEG-DB concentration in the glycolide after the bubbling was 1,500 ppm, and the hexane concentration was 30 ppm.

The residual solvent concentrations after each of Steps 1-3 in the above-mentioned Examples 1-6 are inclusively shown in the following Table 1.

TABLE 1

| | | Step 1 | Step 2 | | | Step 3 | |
| | | | Solvent | | | | |
| | | | Residual | Removed | | | |
| | Solvent name | Solvent [ppm] | amount [ppm] | amount [ppm] | Hexane [ppm] | Solvent [ppm] | Hexane [ppm] |
|---|---|---|---|---|---|---|---|
| Example 1 | DEG-DB | 4,500 | 900 | 3,600 | 4,200 | 900 | 30 |
| Example 2 | TEG-BH | 4,500 | 2,200 | 2,300 | 4,000 | 2,200 | 30 |
| Example 3 | TEG-BO | 3,900 | 270 | 3,630 | 4,000 | 290 | 30 |
| Example 4 | TEG-BD | 700 | 400 | 300 | 4,200 | 410 | 30 |
| Example 5 | DEG-BClPh | 16,000 | 4,500 | 11,500 | 4,000 | 4,500 | 30 |
| Example 6 | TEG-DB | 10,000 | 1,500 | 8,500 | 4,000 | 1,500 | 30 |

Example 7

[Steps 1-3]

Steps 1-3 were performed similarly as in Example 3. The resultant glycolide contained 300 ppm of TEG-BO, less than 10 ppm of hexane, and a glycolide purity of 90.00% according to the GC analysis.

[Step 4]

The glycolide obtained in Step 3 was continuously supplied to a horizontal multistage cooling crystallizer (Cooling Disk Crystallizer) [made by Gauda Co. in the Netherlands] having an apparatus volume of 1 m$^3$ and cooled to 70.0° C. to be crystallized, thereby obtaining a slurry at a crystallization rate of 25%.

[Step 5]

The slurry obtained in Step 4 was supplied to a vertical centrifuge of 24 inches in basket inner diameter to effect 16 minutes of liquid removal at 1600 rpm, thereby recovering the crystals of the glycolide. The recovered glycolide exhibited a purity of 99.15% and less than 10 ppm each of TEG-BO concentration and hexane concentration.

[Step 6]

The crystal of the glycolide obtained in Step 5 was charged into a column-type crystal refiner comprising two cylindrical columns each having an inner diameter of 200 mm and a height of 5300 mm combined and superposed with each other (in a form as disclosed in a JP-A 2001-278877) at a rate of 20 kg/h, whereby refined glycolide was obtained from the column top at a rate of 15 kg/h, and at a yield of 20% with respect to the amount of glycolide obtained in Step 1. The resultant glycolide exhibited a purity of 99.90 mol. % according to DSC measurement, and less than 10 ppm each of TEG-BO concentration and hexane concentration.

Example 8

[Steps 1-4]

Steps 1-4 were performed similarly as in Example 7.

(Step 5)

The slurry obtained in Step 4 was supplied to a vertical centrifuge of 24 inches in basket inner diameter to effect 3 minutes of liquid removal at 1600 rpm and, while maintaining 1600 rpm, molten liquid of purified glycolide at a purity of at least 99.9% and in an amount of 30 wt. % of the glycolide crystal in the basket was sprayed onto the glycolide crystal in the basket, followed by further 13 minutes of liquid removal, to obtain purified glycolide at a yield of 25% based on the glycolide after Step 1. The resultant glycolide exhibited a purity of 99.90 mol. % according to DSC measurement, and less than 10 ppm each of TEG-BO concentration and hexane concentration.

Comparative Example

The glycolide obtained in Step 1 of Example 3 and solidified by cooling was charged into a column-type crystal refiner comprising two cylindrical columns each having an inner diameter of 37.5 mm and a height of 1000 mm combined and superposed with each other (as disclosed in JP-A 2001-278877) at a rate of 15 g/h, and the refined glycolide at a purity of 97% was obtained from the column top at a yield of 53% at 8 g/h. The TEG-BO concentration in the obtained refined glycolide was 2,550 ppm.

[INDUSTRIAL APPLICABILITY]

As described above, according to the present invention, there is provided a method of purifying a cyclic ester, comprising: subjecting a co-distillated liquid comprising a cyclic ester produced by heating depolymerization of a hydroxycarboxylic acid oligomer in the presence of a depolymerization solvent and the depolymerization solvent to washing with a low-boiling point organic solvent and evaporation the organic solvent, to recover a refined cyclic ester at high heat efficiency, purification efficiency and operation efficiency.

The invention claimed is:

1. A method of purifying a cyclic ester, comprising, sequentially:
   (Step 1) subjecting a co-distillated liquid comprising a cyclic ester produced by heating depolymerization of a hydroxycarboxylic acid oligomer in the presence of a depolymerization solvent and the depolymerization solvent to liquid-liquid separation separating the co-distillated liquid into a depolymerization solvent phase and a cyclic ester phase containing the depolymerization solvent;
   (Step 2) mixing the resultant cyclic ester phase containing the depolymerization solvent with an organic solvent for washing which is mutually soluble with the depolymerization solvent and has a lower boiling point than the cyclic ester; and subjecting the resultant mixture liquid to liquid-liquid separation into an organic solvent phase containing the depolymerization solvent and a cyclic ester phase containing the organic solvent; and
   (Step 3) evaporating the organic solvent from the cyclic ester phase containing the organic solvent to recover the cyclic ester having a reduced amount of the depolymerization solvent.

2. The purification method according to claim 1, wherein the depolymerization solvent is a polyalkylene glycol ether.

3. The purification method according to claim 2, wherein the polyalkylene glycol ether has 2-8 repeating alkylene-oxy groups and includes ether oxygen-bonded groups at both ends each comprising an alkyl group having 3- 21 carbon atoms.

4. The purification method according to claim 3, wherein the polyalkylene glycol ether has a boiling point (under normal pressure) of 230-450° C.

5. The purification method according to claim 1, wherein the organic solvent for washing has a boiling point (under normal pressure) of at most 90° C.

6. The purification method according to claim 5, wherein the organic solvent for washing is hexane.

7. The purification method according to claim 1, wherein the co-distillate is washed with the organic solvent for washing at 85-150° C.

8. The purification method according to claim 1, including a step of subjecting the recovered cyclic ester having a reduced amount of the depolymerization solvent to crystallization, and after solid liquid separation, a step of washing the crystal with a molten liquid of refined cyclic ester.

9. The purification method according to claim 1, wherein the cyclic ester is glycolide.

* * * * *